US009572962B2

(12) United States Patent
Scholz

(10) Patent No.: US 9,572,962 B2
(45) Date of Patent: Feb. 21, 2017

(54) MEDICAL DRESSINGS WITH VALVE AND KITS CONTAINING SAME

(75) Inventor: Matthew T. Scholz, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1372 days.

(21) Appl. No.: 12/936,273

(22) PCT Filed: Apr. 1, 2009

(86) PCT No.: PCT/US2009/039149
§ 371 (c)(1),
(2), (4) Date: Jan. 5, 2011

(87) PCT Pub. No.: WO2009/124125
PCT Pub. Date: Oct. 8, 2009

(65) Prior Publication Data
US 2011/0106030 A1    May 5, 2011

Related U.S. Application Data

(60) Provisional application No. 61/042,338, filed on Apr. 4, 2008.

(51) Int. Cl.
*A61M 1/00* (2006.01)
*A61M 27/00* (2006.01)
*A61M 35/00* (2006.01)
*A61F 13/00* (2006.01)

(52) U.S. Cl.
CPC ........... *A61M 27/00* (2013.01); *A61M 1/0031* (2013.01); *A61M 1/0088* (2013.01); *A61M 2205/3334* (2013.01)

(58) Field of Classification Search
CPC .. A61M 27/00; A61M 1/0031; A61M 1/0088; A61M 2205/3334
USPC .......................... 604/289, 304, 319; 128/156
See application file for complete search history.

(56) References Cited

U.S. PATENT DOCUMENTS

| RE24,906 | E | 12/1960 | Ulrich |
|---|---|---|---|
| 3,389,827 | A | 6/1968 | Abere et al. |
| 3,645,835 | A | 2/1972 | Hodgson |
| 4,112,213 | A | 9/1978 | Waldman |
| 4,310,509 | A | 1/1982 | Berglund et al. |
| 4,323,557 | A | 4/1982 | Rosso et al. |
| 4,472,480 | A | 9/1984 | Olson |
| 4,485,809 | A | 12/1984 | Dellas |

(Continued)

FOREIGN PATENT DOCUMENTS

| EP | 0 051 935 B1 | 11/1986 |
|---|---|---|
| WO | WO 03/045492 A1 | 6/2003 |
| WO | WO 2008/015574 A2 | 2/2008 |

OTHER PUBLICATIONS

PCT Internationat Search Report.
(Continued)

*Primary Examiner* — Tatyana Zalukaeva
*Assistant Examiner* — Andrew J Mensh

(57) ABSTRACT

Medical dressings and medical dressing kits that can be used to provide negative pressure wound therapy. The medical dressings include one or more normally-closed valves, and may include stand-off elements, barrier elements, closure elements, and septum elements. The medical dressing kits may further include pumps, fluid traps, and/or fittings.

13 Claims, 7 Drawing Sheets

(56) References Cited

U.S. PATENT DOCUMENTS

| | | |
|---|---|---|
| 4,541,426 A | 9/1985 | Webster |
| 4,595,001 A | 6/1986 | Potter et al. |
| 4,598,004 A | 7/1986 | Heinecke |
| 4,600,001 A | 7/1986 | Gilman |
| 4,737,410 A | 4/1988 | Kantner |
| 4,969,880 A | 11/1990 | Zamierowski |
| 5,086,763 A | 2/1992 | Hathman |
| 5,088,483 A | 2/1992 | Heinecke |
| 5,160,315 A | 11/1992 | Heinecke et al. |
| 5,160,322 A | 11/1992 | Scheremet et al. |
| 5,261,893 A | 11/1993 | Zamierowski |
| 5,478,333 A | 12/1995 | Asherman, Jr. |
| 5,527,293 A | 6/1996 | Zamierowski |
| 5,803,086 A | 9/1998 | Scholz et al. |
| 5,979,450 A | 11/1999 | Baker et al. |
| 6,071,267 A | 6/2000 | Zamierowski |
| 6,169,224 B1 | 1/2001 | Heinecke et al. |
| 6,420,622 B1 | 7/2002 | Johnston et al. |
| 6,539,691 B2 | 4/2003 | Beer |
| 6,607,764 B1 | 8/2003 | Keller |
| 6,685,682 B1 | 2/2004 | Heinecke et al. |
| 6,733,803 B1 | 5/2004 | Vidkjaer |
| 6,742,522 B1 | 6/2004 | Baker et al. |
| D493,230 S | 7/2004 | Liedtke et al. |
| 6,867,342 B2 | 3/2005 | Johnston et al. |
| 6,893,655 B2 | 5/2005 | Flanigan et al. |
| 6,913,803 B2 | 7/2005 | Peper |
| 6,994,904 B2 | 2/2006 | Joseph et al. |
| 7,216,651 B2 | 5/2007 | Argenta et al. |
| 7,699,823 B2 * | 4/2010 | Haggstrom et al. .......... 604/313 |
| 7,777,397 B2 | 8/2010 | Bharti |
| 7,951,124 B2 * | 5/2011 | Boehringer et al. .......... 604/319 |
| 2004/0260253 A1 * | 12/2004 | Rosati ........................... 604/289 |
| 2006/0025787 A1 | 2/2006 | Morales et al. |
| 2006/0228057 A1 | 10/2006 | Newrones et al. |
| 2007/0055209 A1 * | 3/2007 | Patel et al. .................... 604/315 |
| 2007/0156075 A1 | 7/2007 | Heinecke |
| 2007/0172157 A1 | 7/2007 | Buchman |
| 2007/0209326 A1 | 9/2007 | Tretina |
| 2007/0233022 A1 | 10/2007 | Henley et al. |
| 2008/0033377 A1 | 2/2008 | Kauth et al. |
| 2010/0286639 A1 | 11/2010 | Scholz |
| 2011/0112492 A1 | 5/2011 | Bharti |

OTHER PUBLICATIONS

PCT Written Opinion of the International Searching Authority.
European Search Report—Supplementary.
Nostrand-Reinhold, Van, Handbook of Pressure Sensitive Adhesive Technology, 1982, pp. 384-403, Chapter 18.

\* cited by examiner

MEDICAL DRESSINGS WITH VALVE AND KITS CONTAINING SAME

CROSS REFERENCE TO RELATED APPLICATIONS

This application is a national stage filing under 35 U.S.C. 371 of PCT/US2009/039149, filed Apr. 1, 2009, which claims priority to U.S. Provisional Application No. 61/042,338, filed Apr. 4, 2008, the disclosures of which are incorporated by reference in their entirety herein.

FIELD OF THE INVENTION

The present invention provides medical dressings and medical dressing kits that can be used to deliver negative pressure wound therapy, more particularly, the present invention provides medical dressings that include one or more normally-closed valves and kits including such dressings.

BACKGROUND

The length of time over which medical dressings may remain in place over wounds may be limited by many factors. Among the factors that may limit the usable life of a medical dressing is the accumulation of fluids within the wound. Some medical dressings have incorporated absorbent materials to increase the time over which the medical dressings may remain in place over wounds. For example, absorbent materials such as hydrocolloids, foams, hydrogels, nonwovens (such as alginates and carboxymethylcelluloses), and combinations thereof have been used to increase the useful life of medical dressings.

Other approaches to increasing useful life of medical dressings have included the use of negative pressure wound therapy in which fluids are removed from the beneath the wound dressings without requiring removal of the dressings from the patient. Dressings adapted for delivery of negative pressure wound therapy (such as those described in, e.g., U.S. Pat. Nos. 4,969,880; 5,261,893; 5,527,293; and 6,071,267 (all to Zamierowski)) often have constructions that can compromise the sterility of the wound over which they are placed. These products often require a tube or wound drain that is introduced either through a multi-piece dressing or under a single piece dressing. In either case, it is difficult (if not impossible) to obtain a good seal between the tube or wound drain and, during treatment, air can leak into the wound. That air can carry contamination into the wound and/or impair the effectiveness of the pressure-based therapy.

U.S. Pat. No. 5,478,333 describes a wound dressing for chest wounds with a one-way valve. The dressing may also be used in conjunction with a "suction producing device" that is inserted into the one-way valve. Negative pressure is applied by inserting the suction-producing device through the valve.

SUMMARY

The present invention provides medical dressings that can be used to provide a sealed environment over a wound or other body site. The medical dressings include one or more normally-closed valves that allow fluids to be removed from the sealed environment. Fluid removed from the sealed environment may include gases and/or liquids (which may contain dispersed solid particles such as necrotic tissue, blood clots, etc.). The fluid removal can be performed through the normally-closed valve without removing or otherwise disturbing the medical dressing.

As used herein, the term "sealed environment" means that fluids (and solids) from the ambient atmosphere surrounding the exterior of a medical dressing attached over a wound cannot freely enter the sealed environment. The sealed environment preferably includes a hermetic seal between the medical dressing and the surface surrounding the wound such that a negative pressure can be maintained in the sealed environment. It may, for example, be preferred that the medical dressing be capable of holding (at least temporarily as described herein) a vacuum of 100 mmHg (i.e., a pressure that is 100 mmHg below atmospheric pressure) and perhaps a vacuum as much as 200 mmHg. Although some conventional medical dressings can provide such a sealed environment, the medical dressings of the present invention can do so while also offering the opportunity to remove fluids (liquids and/or gases) from the sealed environment through a valve provided as a part of the medical dressing.

The valves provided in connection with the medical dressings of the present invention preferably have a relatively low profile or height. The low profile of the valves preferably reduces the likelihood that the medical dressing will be disturbed by external forces (from, e.g., bedding, clothing, etc.). The low profile valves may also improve patient comfort where, for example, the dressing is placed in a location on which the patient's weight rests while sitting, lying, and/or standing. As discussed herein, the low-profile nature of the valves may be characterized in terms of dead volume defined by the valve and the backing, the height or thickness of the valve, etc. The valves used in the medical dressings of the invention may also preferably be soft and conformable such that they provide a reduced likelihood of creating a pressure point that could, e.g., cause wound damage if a patient were lying on the portion of the dressing containing the valve for prolonged periods of time (e.g., two hours or more). Preferred valves may be so conformable that the valve, even as attached to the dressing, can be manually folded over between the thumb and the forefinger of a person such as a healthcare worker in at least one direction and preferably in multiple directions. The most preferred valves will recover fully from folding. These preferred valves are comprised of a laminate of at least two film layers.

Fluid removal from the sealed environment may be useful to provide negative or reduced pressure therapies to a wound over which the medical dressing is located. With the use of a suitable valve, the sealed environment created by a medical dressing of the present invention may preferably be maintained at a negative pressure (i.e., pressure below the ambient atmospheric pressure) in the absence of active vacuum source in fluid communication with the sealed environment. In other words, the medical dressings of the present invention may be used to maintain a sealed environment with a negative or reduced pressure in the periods between active removal of fluids from the sealed environment. As a result, the medical dressings can provide a negative or reduced pressure environment with only intermittent or periodic fluid removal.

Although the magnitude of the negative pressure maintained in the sealed environment by the medical dressings will typically deteriorate over time (after reaching a maximum during that active removal of fluids from the sealed environment), it may be preferred that the medical dressing be capable of maintaining the negative pressure for at least some significant period of time. In some embodiments, it may be preferred that the medical dressing be capable of maintaining at least some level of negative pressure in the sealed environment (in the absence of active fluid removal) for a period of 1 minute or more, 5 minutes or more, 10 minutes or more, 15 minutes or more, 30 minutes or more, or even 60 minutes or more.

Deterioration of the negative pressure within the sealed environment defined by the medical dressing may be caused by a variety of sources. For example, some of the deterioration may be due to the diffusion of gas into the sealed environment through the backing of the medical dressing and/or the adhesive attaching the medical dressing to a subject. Another source of negative pressure deterioration in the sealed environment may be caused by gases and/or liquids entering the sealed environment from the subject (i.e., through the wound itself and/or the tissue surrounding the wound).

To retain a negative pressure within the sealed environments, it may be preferred that the normally-closed valves used with the medical dressings be one-way valves. In other words, it may be preferred that the valve allow fluid flow in one direction (out of the sealed environment) and restrict or prevent flow in the opposite direction (into the sealed environment).

In various embodiments, the medical dressings may include stand-off elements to provide open fluid pathways to the valves (that resist closing under negative pressure in the sealed environment), barrier elements (to limit clogging of the valves); septum elements, and/or closure elements. The closure elements may, in some instances, be provided over the valves, such that the valves are sealed shut until the closure elements are removed.

The closure elements may be adhesively attached such that they can be relocated to a different site on the medical dressing (after removal from the valve) or they may be replaced over the valve after, e.g., fluids are removed from the sealed environment to ensure proper closure of the valve and/or reduce unwanted leakage of fluids out of the sealed environment created by the medical dressing. In some embodiments, the use of a closure element over the valve may offer the flexibility of: a) a conventional medical dressing (i.e., one that does not include any valves and thus has substantially no likelihood of unwanted leakage), and b) a medical dressing that is adapted for use with negative pressure wound therapy by offering a valve to allow for fluid removal from the sealed environment defined by the medical dressing.

Among the potential advantages that may be associated with use of the medical dressings of the invention is that, in some instances, the negative pressure may advantageously pull the edges of acute incisional wounds together, thus potentially providing faster healing, reduced infection rates, and/or improved cosmetic results (reduced scarring).

In one aspect, the present invention provides a medical dressing comprising a backing comprising an interior surface and an external surface; adhesive on at least a portion of the interior surface, wherein the adhesive extends around a perimeter of the interior surface of the backing to adhere the medical dressing to a subject over a wound; a normally-closed valve attached to the backing over an opening formed through the backing, wherein fluid flow through the opening is controlled by the valve, and wherein a dead volume between the normally-closed valve and the backing is 10 mm$^3$ or less; wherein, when the medical dressing is attached over the wound, the medical dressing defines a sealed environment over the wound, and further wherein application of a vacuum to the external surface of the backing over the valve opens the normally-closed valve such that fluid within the sealed environment can be removed through the opening in the backing.

In another aspect, the present invention provides a medical dressing comprising a backing comprising an interior surface and an external surface; a normally-closed valve attached to the backing over an opening formed through the backing, wherein fluid flow through the opening is controlled by the valve, and wherein a dead volume between the normally-closed valve and the backing is 6 mm$^3$ or less; wherein, when the medical dressing is attached over the wound, the medical dressing defines a sealed environment over the wound, and further wherein application of a vacuum to the external surface of the backing over the valve opens the normally-closed valve such that fluid within the sealed environment can be removed through the opening in the backing.

In another aspect, the present invention may provide a medical dressing comprising a backing comprising an interior surface and an external surface; adhesive on at least a portion of the interior surface, wherein the adhesive extends around a perimeter of the interior surface of the backing to adhere the medical dressing to a subject over a wound; a normally-closed valve attached to the backing over an opening formed through the backing, wherein fluid flow through the opening is controlled by the valve, wherein the valve comprises a plurality of polymeric film layers aligned with the backing when in a closed configuration, and wherein the plurality of polymeric film layers comprises a flap layer comprising a flap formed therein, wherein the flap is not aligned with the backing when the valve is in an open configuration; wherein, when the medical dressing is attached over the wound, the medical dressing defines a sealed environment over the wound, and further wherein application of a vacuum to the external surface of the backing over the valve opens the normally-closed valve such that fluid within the sealed environment can be removed through the opening in the backing.

In another aspect, the present invention may provide a medical dressing comprising a backing comprising an interior surface and an external surface; adhesive on at least a portion of the interior surface, wherein the adhesive extends around a perimeter of the interior surface of the backing to adhere the medical dressing to a subject over a wound; a normally-closed valve attached to the backing over an opening formed through the backing, wherein fluid flow through the opening is controlled by the valve, wherein the valve comprises a maximum thickness as measured normal to the interior surface and the external surface of the backing of one centimeter or less; wherein, when the medical dressing is attached over the wound, the medical dressing defines a sealed environment over the wound, and further wherein application of a vacuum to the external surface of the backing over the valve opens the normally-closed valve such that fluid within the sealed environment can be removed through the opening in the backing.

In some embodiments such as those provided above, the medical dressing further comprises a stand-off element, wherein the stand-off element defines plurality of fluid pathways to the opening on the interior surface of the backing when the stand-off element is positioned proximate the interior surface of the backing in the sealed environment. Further in some embodiments such as those provided above, the stand-off element comprises a separate article attached to the interior surface of the backing, and further wherein the stand-off element comprises fluid pathway-forming structures on two major surface of the separate article.

Any of the above embodiments may also comprise one or more of the following elements in any combination: a septum element, a closure element, a barrier element, wound packing material, a pump, and/or a fluid trap.

In another aspect, the present invention provides a medical dressing kit, the kit comprising a medical dressing according to any one of the embodiments provided above; a stand-off element that defines plurality of fluid pathways to the opening on the interior surface of the backing when the stand-off element is positioned proximate the interior surface of the backing in the sealed environment; optionally, a septum element; optionally, a closure element; optionally, a barrier element; optionally, wound packing material; optionally, a pump; optionally, a fluid trap; and optionally, a fitting adapted for attachment to the external surface of the backing over the valve.

In various embodiments, the methods may include one or more of the following features: A method of treating a wound, the method comprising applying a medical dressing over a wound according to any one of embodiments such as those provided above; and removing fluid from the sealed environment through the valve in the medical dressing. In some embodiments such as those provided above, the method of removing fluid from the internal volume comprises air such that the pressure within the sealed environment is below atmospheric pressure the method of removing fluid from the internal volume comprises wound exudate from the wound.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. The term "and/or" (if used) means one or all of the identified elements/features or a combination of any two or more of the identified elements/features.

The term "and/or" means one or all of the listed elements/features or a combination of any two or more of the listed elements/features.

The above summary is not intended to describe each embodiment or every implementation of the present invention. Rather, a more complete understanding of the invention will become apparent and appreciated by reference to the following Description of Exemplary Embodiments and claims in view of the accompanying figures of the drawing.

BRIEF DESCRIPTIONS OF THE DRAWING

The present invention will be further described with reference to the views of the drawing, wherein.

DESCRIPTION OF EXEMPLARY EMBODIMENTS

Figure 1:
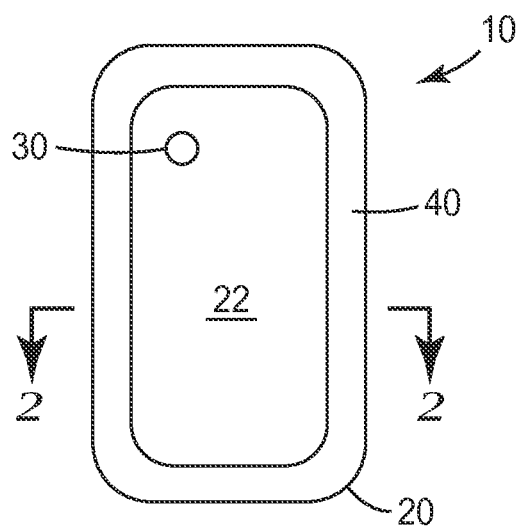
FIG. 1 is a plan view of one embodiment of a medical dressing according to the present invention.

In the following description of exemplary embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

Figure 2:
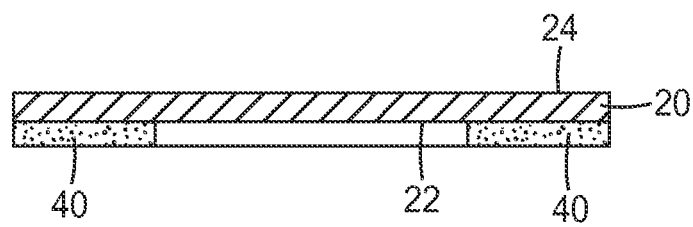
FIG. 2 is a cross-sectional view of the medical dressing of FIG. 1 taken along line 2-2 in FIG. 1.

One exemplary embodiment of a medical dressing according to the present invention is depicted in FIGS. 1 and 2 (where FIG. 2 is a cross-sectional view taken along line 2-2 in FIG. 1). The medical dressing 10 includes a backing 20 (which may preferably be conformable as described herein). The backing 20 includes two opposed major surfaces: an interior surface 22 and an external surface 24. In use, the interior surface 22 faces a wound (or other body site) over which the dressing is placed while the external surface 24 faces away from the wound (or other body site).

Potentially suitable materials for the backing 20 are described in more detail below, but functionally, the backing 20 is preferably made of materials that serve as a barrier to both liquid and rapid gas diffusion. The barrier properties of the backing 20 may or may not be absolute, e.g., the backing 20 may allow for limited passage of gas, although the backing 20 (and the other components of the dressing 10) preferably provide sufficient barrier properties to the passage of gas such that, when placed over a wound, a negative pressure environment can be at least temporarily maintained above a wound. For example, the backings may preferably have relatively high moisture vapor transmission rates, but be substantially impervious to liquids.

The dressing 10 further includes a normally-closed valve 30 that is attached to the backing 20 over one or more passages that are formed through the backing 20. Fluid flow through the one or more passages in the backing 20 is controlled by the valve 30. The valve 30 (preferably be a one-way valve) may be used to provide negative pressure therapy to a wound over which the dressing 10 is placed as described herein. Although the medical dressing depicted in FIGS. 1 and 2 includes only one valve 30, medical dressings of the present invention may include more than one valve if additional access to the sealed environment defined by the dressing is desired.

Figure 3:
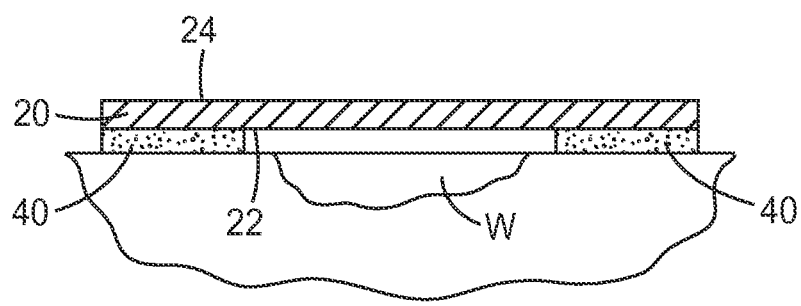
FIG. 3 is a cross-sectional view of the medical dressing of FIGS. 1 and 2 located over a wound W.

The dressing 10 may also include an adhesive 40 on the interior surface 22 such that the dressing 10 can be adhered to a subject over a wound with the interior surface 22 facing a wound. The adhesive 40 may cover all or part of the interior surface 22 in a continuous and/or pattern coated fashion. The adhesive 40 as depicted in FIG. 2 is provided only around the perimeter or border of the backing 20 such that the adhesive 40 forms a frame around a central part of the interior surface 22 of the backing 20. Many other arrangements are possible including dressings that are secured without the need for pressure sensitive adhesives. For example, the dressing may comprise a circumferential wrap around a limb which would not necessarily require an adhesive. One arrangement is depicted in FIG. 3 in which the dressing 10 is located over a wound W while the adhesive 40 is attached to the tissue (e.g., skin) surrounding the wound W. The dressing 10, along with the wound W and the tissue surrounding the wound, preferably define a sealed environment in which the wound W is isolated from the surrounding environment. The interior surface 22 of the backing 20 faces the sealed environment in which the wound is located while the external surface 24 of the backing 20 faces away from the wound W.

The adhesive 40 as depicted in FIGS. 1 and 2 may preferably be exposed on only a portion of the interior surface 22 of the backing 20. In the embodiment depicted in FIGS. 1 and 2, the adhesive 40 is provided on only a portion of the interior surface 22 (i.e., the central portion of the interior surface 22 is free of the adhesive 40). In other embodiments, however, adhesive may be provided over substantially all of the interior surface 22 with a portion of the adhesive covered by another element such that only a portion of the adhesive remains exposed for attachment to a subject.

In any embodiment, however, it may be preferred that the adhesive 40 extend continuously around the entire perimeter of the backing 20 such that the dressing 10, when attached to a subject, can form a sealed environment over a wound, with the bounds of the sealed environment being defined by the interior surface 22 of the backing 20 as adhered to the subject over a wound by the adhesive 40.

With the use of a suitable valve 30, the sealed environment created by a dressing 10 attached over a wound may preferably be maintained at a negative pressure (i.e., pressure below the ambient atmospheric pressure on the external surface 24 of the backing 20) in the absence of active vacuum source in fluid communication with the sealed environment.

It may be preferred that the valves used in connection with the present invention be capable of being used one, two or more times to remove fluids from the sealed environment without requiring that the medical dressing be removed and without requiring the constant removal of fluid to maintain a negative pressure within the sealed environment. For example, fluid can be removed from the sealed environment through the valve as described herein, with the valve being allowed to close when the fluid removal terminates. As additional fluid accumulates in the sealed environment, it can be removed through the valve as described herein. In some embodiments, it may be preferred that the medical dressing include absorbent material to absorb fluids (e.g., liquids) entering the sealed environment. Examples of potentially suitable absorbent materials may include, but are not limited to, hydrophilic foams, woven materials, nonwoven materials, etc. and combinations thereof. It may be preferred that the absorbent material be both absorbent and capable of releasing at least some (preferably a majority) of any absorbed fluids when a vacuum is applied to the sealed environment through a valve. By releasing absorbed fluids during the removal of fluids from the sealed environment, the ability of the absorbent material to absorb fluids may be regenerated—which may prolong the useful life of the medical dressing.

Although the magnitude of the negative pressure maintained in the sealed environment by the dressing 10 will typically deteriorate over time (after reaching a maximum during that active removal of fluids from the sealed environment through the valve 30), it may be preferred that the dressing 10 be capable of maintaining the negative pressure for at least some significant period of time. In some embodiments, it may be preferred that the dressing 10 be capable of maintaining at least some level of negative pressure in the sealed environment (in the absence of active vacuum source) for a period of 1 minute or more, 5 minutes or more, 10 minutes or more, 15 minutes or more, 30 minutes or more, or even 60 minutes or more.

Deterioration of the negative pressure within the sealed environment defined by the dressing 10 may be caused by a variety of sources. For example, some of the deterioration may be due to the diffusion of gas into the sealed environment through the backing 20 and/or the adhesive 40 attaching the backing 20 to the subject. Another source of negative pressure deterioration in the sealed environment may be caused by gases and/or liquids entering the sealed environment from the subject (through the wound itself and/or the tissue surrounding the wound).

Maintenance of the negative pressure within the sealed environment may, in some embodiments, be enhanced by the addition of a ballast component within the sealed environment. A ballast component may be a resiliently compressible material that, e.g., compresses or shrinks as a vacuum (negative pressure) is provided within the sealed environment and that attempts to return to at least a portion of its pre-compression size because of its resilient nature. For example, the ballast component may be a resilient foam (open or closed cell, although preferably open cell), nonwoven material, spring, or other structure that can be compressed, but that also is resilient such that it will attempt to return to at least a portion of its pre-compressed size (e.g., the resilient material has a spring constant).

Figure 4A:
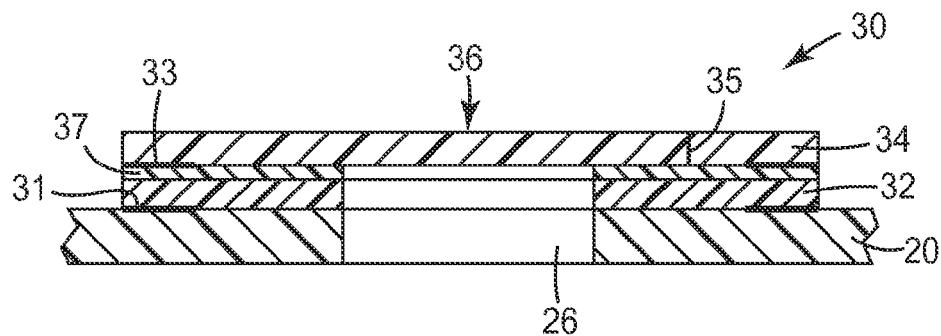
FIG. 4A is an enlarged cross-sectional view of one exemplary valve that may be used in a medical dressing of the present invention, wherein the valve is in a closed configuration.
Figure 4B:
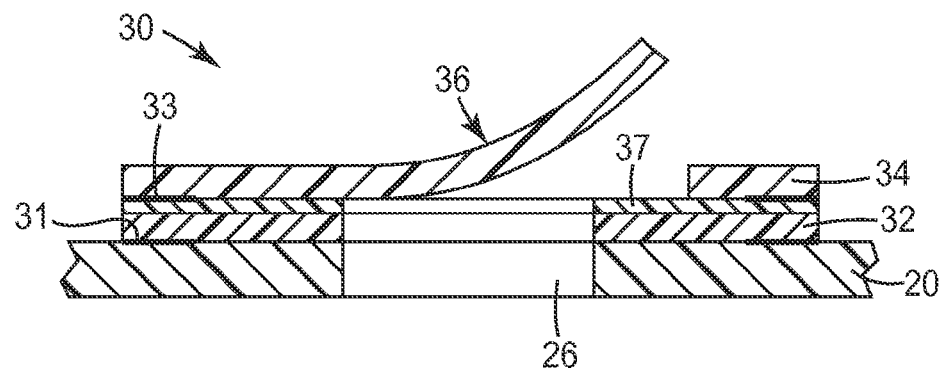
FIG. 4B is an enlarged cross-sectional view of the valve of FIG. 4A in an open configuration.
Figure 4C:
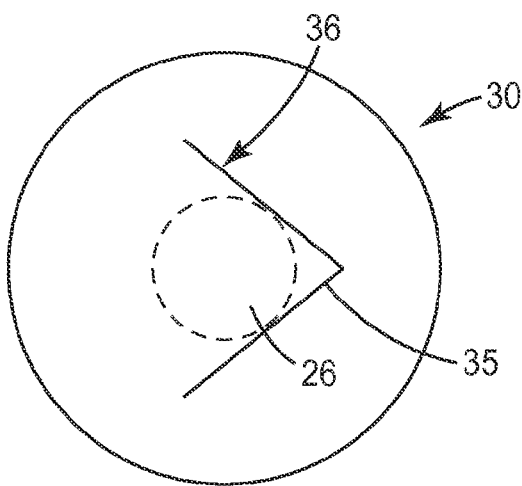
FIG. 4C is a plan view of the external surface of the valve of FIGS. 4A and 4B.

One exemplary embodiment of a valve 30 that may be used in a medical dressing 10 as depicted in FIGS. 1-3 is found in FIGS. 4A-4C. Although this valve represents one embodiment of a potentially suitable valve that may be used in connection with the present invention, many other valves may be used in place of the specific valve structure depicted in FIGS. 4A-4C.

The valve 30 of FIGS. 4A-4C is depicted as being located over a single opening 26 formed through the backing 20, although the valve 30 may be located over two or more openings to control fluid flow through the openings. As discussed herein, the valve 30 and the opening 26 may preferably provide an evacuation port through which fluids can pass through the backing 20. The valve 30 includes a base layer 32 attached to the backing 20 and a flap layer 34 attached to the base layer 32 such that the base layer 32 is located between the flap layer 34 and the backing 20.

The base layer 32 may be attached to the backing 20 by any suitable technique or combination of techniques, e.g., adhesives, heat sealing, chemical welding, thermal welding, ultrasonic welding, etc. In the depicted embodiment, the base layer 32 is attached to the backing 20 using adhesive 31. The flap layer 34 may be attached to the base layer 32 by any suitable technique or combination of techniques, e.g., adhesives, heat sealing, chemical welding, thermal welding, ultrasonic welding, etc. In the depicted embodiment, the flap layer 34 may be attached to the base layer 32 by adhesive 33 that may preferably be located proximate the outer perimeters of the base layer 32 and the flap layer 34. The valve 30 may also include optional seating adhesive 37 on the area of the base layer 32 against which the valve flap 36 rests when in the closed position. The seating adhesive 37 may preferably have limited tack to allow opening of the valve 30 as discussed herein, but may also improve sealing of the valve 30 when in the closed configuration.

The flap layer 34 includes a slit 35 that defines the shape of a valve flap 36 in the flap layer 34. The valve flap 36 may preferably have a closed configuration in which the valve flap 36 is located over the opening 26 in the backing 20 to close the opening 26 such that fluid cannot freely pass through the opening 26 (see FIG. 4A). If present, the seating adhesive 37 may assist in sealing the valve 30. The valve flap 36 is preferably moveable to transform the valve 30 from the closed configuration of FIG. 3A to an open configuration in which fluids can pass through the opening 26 and the valve 30 (as depicted in FIG. 4B).

Transformation of the valve 30 between the open and closed configurations may preferably be performed selectively, although it may be preferred that the valve 30 be normally closed such that, in the absence of an applied force capable of opening the valve 30, the valve 30 is closed. In some embodiments, the valve 30 may be opened by a pressure differential placed across the valve 30 (i.e., across the backing 20 from the interior surface 22 to the external surface 24). For example, the valve flap 36 may be opened when the fluid pressure on the side of the valve 30 facing in the same direction as the interior surface 22 is sufficiently larger than the forces operating on the valve flap 36 to retain it in the closed configuration. The pressure differential at which the valve 30 moves from the closed configuration to the open configuration may be referred to as the "cracking pressure".

The pressure differential across the valve 30 may be achieved by, e.g., applying the inlet of a pump (e.g., a vacuum pump) or a fluid conduit (e.g., tube, hose, etc.) leading to the inlet of a pump over the external surface of valve 30 on the external surface 24 of the backing 20. The pump is preferably capable of providing a reduced pressure environment on the external side of the valve 30 such that the pressure differential across the valve 30 (i.e., between the interior surface 22 and the external surface 24 of the backing 20) is high enough to reach the cracking pressure. Once the valve 30 is in the open configuration, fluids (gases and/or liquids) in the sealed environment defined by the dressing 10 over the wound may be removed through the opening 26 and valve 30. The fluids removed from the sealed environment may or may not contain solid particles.

It may be preferred, but not required, that the fluid removal place the sealed environment at a negative pressure as discussed herein, although such a condition is not necessarily required. For example, the fluid removal may be limited to removing fluids such as wound exudate, blood, etc. from the sealed environment without necessarily resulting in a negative pressure condition within the sealed environment.

The valve 30 depicted in FIGS. 4A-4C is only one example of a potentially suitable valve that may be used in connection with the present invention. Some examples of other potentially suitable valves are depicted in FIGS. 5A-5C.

Figure 5A:
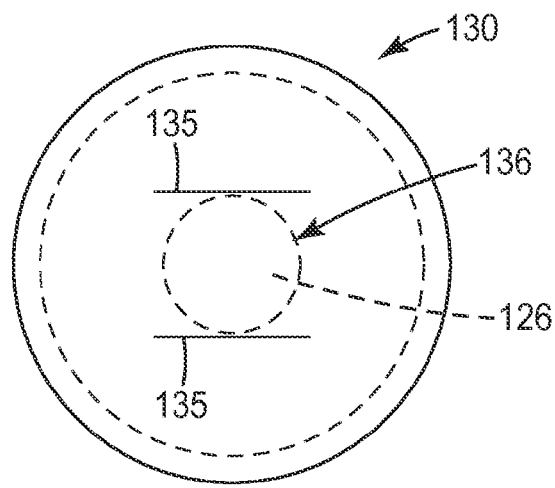
FIG. 5A is a plan view of the external surface of another exemplary valve that may be used in a medical dressing of the present invention.
Figure 5B:
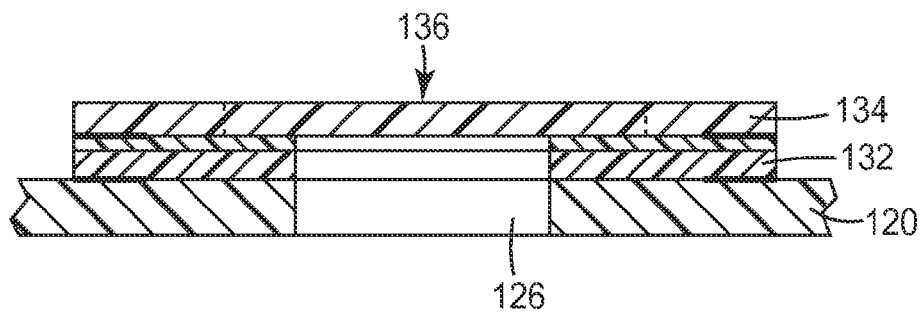
FIG. 5B is an enlarged cross-sectional view of the valve of FIG. 5A, wherein the valve is in a closed configuration.
Figure 5C:
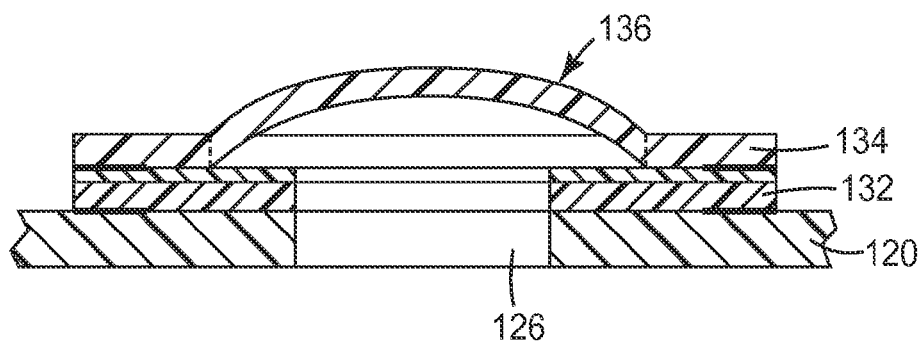
FIG. 5C is an enlarged cross-sectional view of the valve of FIG. 5A, wherein the valve is in an open configuration.

Although the valve 30 of FIGS. 4A-4C includes a valve flap 36 formed by a single continuous slit 35, the valve flaps can be formed by multiple slits as depicted in FIG. 5A. The valve 130 includes a valve flap 136 formed by slits 135 in the flap layer 134. The slits 135 preferably allow the valve flap 136 to lift away from the base layer 132 to allow fluids to pass through opening 126 in the backing 120 on which the valve 130 is located. FIG. 5B depicts the valve 130 in its closed configuration, with the valve flap 136 seated against the base layer 132, while FIG. 5C depicts the valve 130 in its open configuration with the valve flap 136 spaced from the base layer 132 such that fluids can pass through the openings formed along the slits 135.

Figure 6A:
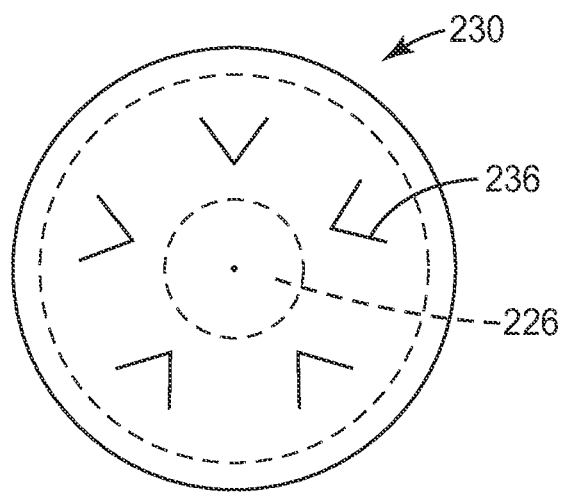
FIGS. 6A and 6B are plan views of two more exemplary valves that may be used in a medical dressing of the invention.
Figure 6B:
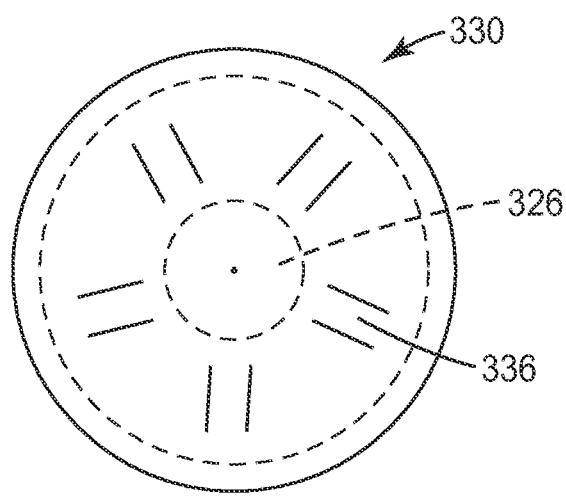

Although the valves 30 and 130 described above each include a single valve flap, the valves used in connection with the present invention may alternatively include two or more valve flaps. Examples of two potentially suitable examples are depicted in FIGS. 6A and 6B, where the valves 230 and 330 each include multiple valve flaps 236 and 336 that open to allow fluids to pass through the openings 226 and 326, respectively.

Valves of the types described above in connection with FIGS. 4A-4C, 5A-5C, and 6A-6B may be characterized as being constructed of a plurality of polymeric film layers. It may further be preferred that the polymeric film layers used in such valves be flexible polymeric films. Additional features and variations, as well as a variety of methods of manufacturing valves such as those described above, may be found in U.S. Patent Application Publication No. US 2006/0228057 (Newrones et al.).

Further, many other valves can be used in place of or in addition to the valves specifically described herein. For example, valves such as those known as "Goglio" type or "Raackmann" type valves may be used in connection with the present invention. Goglio-type valves are available, for example, from Bosch, Wipf, and Wico; Raackmann-type valves are available, for example, from Amcor. Other potentially suitable valves may include duckbill or umbrella valves (examples of which are those available from Vernay Laboratories, Inc., Yellow Springs, Ohio). Still other examples of suitable vacuum valves may include those described in U.S. Pat. Nos. 6,913,803; 6,733,803; 6,607,764; and 6,539,691, each of which is incorporated herein by reference in its entirety.

As discussed herein, it may be preferred that the profile or height of the valves be limited to improve comfort, increase resistance to displacement by external forces (from, e.g., bedding, clothing, etc.).

One manner in which the low-profile valves used in connection with the medical dressings of the present invention can be characterized may be in terms of maximum thickness of the valve structure as measured normal to the major surfaces of the backing (where the major surfaces of the backing are the interior surface and the external surface). It may be preferred, for example, that the valves used in the medical dressings of the present invention have a maximum thickness of 1 centimeter (cm) or less, in some embodiments 5 millimeters (mm) or less, in some embodiments 3 millimeters (mm) or less, or even 2 mm or less, and more preferably 1 mm or less, e.g., even 200 micrometers (μm) or less.

Another manner in which the low-profile valves used in connection with the present invention can be characterized may be in the form of dead volume between the normally-closed valve and the backing. As used herein, the term "dead volume" describes the volume or space in which fluids may accumulate between the valve and the interior surface of the backing when the valve is in its normally-closed configuration. Reducing the dead volume between the normally-closed valve and the interior surface of the backing can help to reduce the profile of the valve and the dressing as a whole.

For example, the valve 30 depicted in FIGS. 4A-4C defines a dead volume that is essentially the space defined by the thickness of the backing 20 (between the interior surface 22 and the external surface 24) and the area occupied in the backing 20 by the opening 26. In this embodiment, the dead volume is further increased by the thickness of the base layer 32 because the valve flap 36 of the flap layer 34 is spaced from the external surface 24 of the backing 20 by the base layer 32.

The dead volume defined by a normally-closed valve and backing in a medical dressing of the present invention may preferably be 200 cubic millimeters ($mm^3$) or less, 100 $mm^3$ or less, 50 $mm^3$ or less, 10 $mm^3$ or less, in some embodiments 6 $mm^3$ or less, or even 4 $mm^3$ or less, and further, in some embodiments, even 2 $mm^3$ or less, e.g. 1 $mm^3$ or less. Dead volume defined by a normally-closed valve may be determined directly, e.g., by measuring the dead volume by filling the valve body with water. Alternatively, where the dead volume is difficult to measure directly, the dead volume may be measured by reference to a separate feature that fits within the dead volume of the valve, and measuring the volume of water displaced by the separate feature. Thus, as an illustration, using a separate feature, such as a catheter hub that fits within the dead volume of a valve, the dead volume of the valve can be approximated by the volume displacement in a 10 ml graduated cylinder by immersing the hub in the water and measuring the volume displacement.

Preferably valve 30 is not incorporated into ports or tubing connections since these connections must be relatively rigid to prevent collapse under vacuum. These rigid structures can cause pressure points when the patient is lying on the wound, for example, when in bed.

Figure 7:
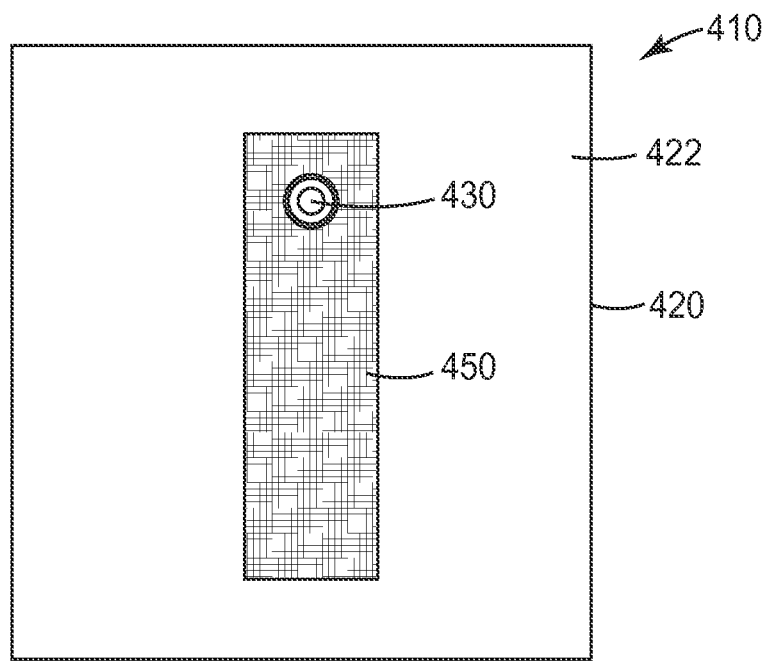
FIG. 7 is a plan view of the interior surface of an exemplary medical dressing including a stand-off element and a valve.

Another optional feature that may be included in some embodiments of the medical dressings of the present invention is a stand-off element that may be located proximate the valve on the interior surface of the backing to assist in the removal of fluids from the sealed environment. FIG. 7 is a plan view of the interior surface 422 of the backing 420 of a medical dressing 410. The medical dressing 410 may include adhesive that is exposed over the entire interior surface 422 except for the area occupied by the stand-off element 450. The adhesive may be continuous or pattern-coated, although regardless of the coating, it may be preferred that the adhesive be capable of providing a hermetic seal such that a negative pressure can be obtained in the sealed environment. One example of a potentially suitable pattern for pattern-coated adhesive may be a grid pattern. It may be preferred that the valve 430 be located within the area of the backing 420 that is occupied by the stand-off element 450, although in some embodiments, the valve 430 may be located proximate the perimeter of the stand-off element 450.

The stand-off element 450 includes some form of structure on one or more surfaces that provides open fluid pathways such that fluids within the sealed environment defined by the medical dressing 410 can be removed through the valve 430. If, for example, a stand-off element 450 is not provided and the interior surface 422 of the dressing 410 were to seal against a wound or the skin surrounding a wound, the removal of fluids from the sealed environment through the valve 430 could be hindered. The stand-off element 450, however, preferably is capable of maintaining open fluid pathways to facilitate fluid removal through the valve 430 even when the sealed environment is at a negative pressure relative to atmosphere, that is, the fluid pathways preferably resist collapsing—even under negative pressure.

Although the medical dressing depicted in FIG. 7 includes only one stand-off element 450 and one valve 430, the medical dressings of the present invention may include, for example, more than one valve in connection with that same stand-off element. The use of multiple valves may be beneficial if, for example, one of the valves is poorly placed relative to the sealed environment, malfunctions, becomes clogged, etc. In another variation, the medical dressings of the present invention may include more than one stand-off element, with each of the stand-off elements potentially associated with one or more valves to facilitate fluid removal from the sealed environment. The use of more than one stand-off element in connection one medical dressing may be beneficial if, for example, one of the stand-off elements is poorly placed relative to the sealed environment, becomes clogged, etc.

The stand-off elements used in the medical dressings of the present invention may take a wide variety of forms. In some embodiments, the stand-off element may be formed directly in the interior surface of the backing (by, e.g., embossing, abrading, molding, cutting, etc.). In other embodiments, the stand-off element take the form of a separate article (e.g., a film, etc.) having channels or other structures embossed, abraded, molded, cut, or otherwise formed therein. The separate article forming the stand-off element may preferably be attached to the backing by any suitable technique or combination of techniques (e.g., adhesives, heat sealing, thermal welding, etc.).

Figure 8:
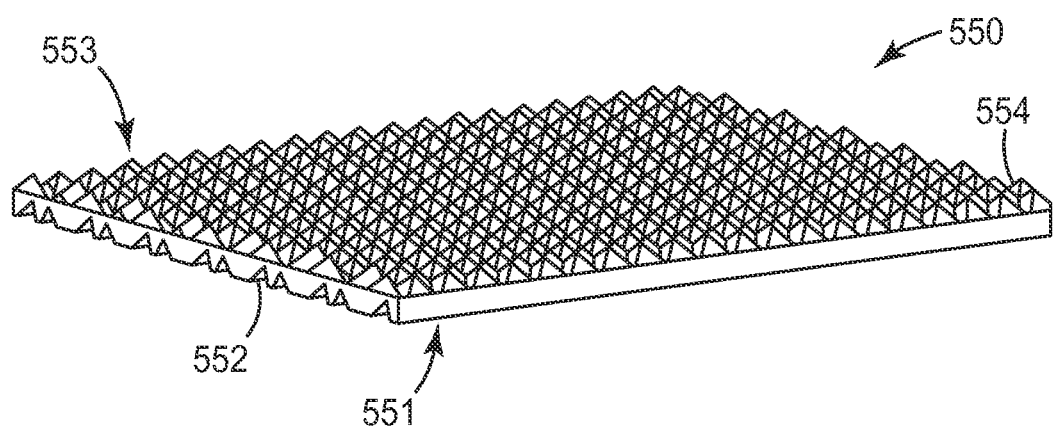
FIG. 8 is a perspective view of another exemplary stand-off element that may be used in connection with a medical dressing of the present invention.

The channels in the stand-off elements may be in any pattern or shape, such as, but not limited to a honeycomb pattern of channels, grid or partial grid, series of grooves (that are, e.g., parallel, radial, etc.), posts or other discrete structures (e.g., pyramids, etc.). In some instances where the stand-off element is provided as an article that is separate from the backing of the medical dressing, the article may include fluid pathway-forming structures on both major sides of the stand-off element. One exemplary embodiment of a dual-sided stand-off element 550 is depicted in FIG. 8 and includes channels 552 and 554 formed into both major sides 551 and 553 (respectively). Examples of some potentially suitable stand-off elements may be further described in, e.g., U.S. Patent Application Publication No. US 2007/0172157 (Buchman), U.S. Pat. No. 6,420,622 (Johnston et al.), etc.

Another optional element that may be included with the medical dressings of the present invention are barrier elements that may be placed proximate the valves of the medical dressings. The barrier elements may preferably function to filter materials from wound exudates that may otherwise cause the valves to become contaminated such that the valves do not re-close or seal after fluids are removed from the sealed environments defined by the medical dressings. The barrier elements may be provided attached to the medical dressings (proximate the interior surfaces of the backings of the medical dressings) or they may be provided with the medical dressings in an unattached form such the barrier elements can be placed during delivery of the medical dressings to a patient. Examples of some materials that may be filtered by the barrier elements may include, e.g., clotted blood, loose tissue, wound packing, etc.

The barrier elements may be provided using a variety of different materials. Examples of some potentially suitable materials for the barrier elements may include, e.g., fabrics (e.g., gauze, nonwoven fabrics, woven fabrics, knitted fabrics, etc.), foams, etc. The barrier elements may also potentially incorporate absorbent materials such as, e.g., hydrogels, hydrocolloids, etc. In some embodiments, the barrier elements may be resiliently compressible, such that the barrier elements can also optionally function as ballast components to assist in maintaining a negative pressure in the sealed environment as described herein.

In some embodiments, the medical dressings may be provided with wound packing material in place of a barrier element or in addition to a barrier element. The wound packing material may, in some embodiments, also function as a barrier element as described herein (although this function is not required). In some embodiments, the wound packing material may be resiliently compressible, such that the wound packing material can also optionally function as a ballast component to assist in maintaining a negative pressure in the sealed environment as described herein. Wound packing materials may be useful where, e.g., the wound to be contained within the sealed environment is a chronic wound that is in the form of a significant depression (which may, in some instances be tunneled under the surrounding skin). When treating such wounds, it may be desirable to provide wound packing material in the wound before applying a medical dressing to create a sealed environment over the wound.

The wound packing may preferably be flexible such that it can fill and/or conform to the shape of the wound. The wound packing may preferably be absorbent or non-absorbent. The wound packing may preferably be capable of providing passageways through which fluids can pass. Some potentially suitable examples of wound packing materials may include fully or partially reticulated foam (e.g., open cell polyurethane foams, etc.), fabric (e.g., gauze, woven, knit, or nonwoven materials), particulate materials, etc. that may be placed in a wound fill the internal volume. If provided in particulate form, the particulates may, in some embodiments, be contained within a flexible bag or other structure to facilitate removal of the wound packing (unless, e.g., the wound packing material is bioabsorbable and/or biodegradable).

If the barrier element and/or wound packing materials are provided in a form such that they are not attached to the medical dressing, the medical dressing may be provided in the form of a kit including the medical dressing and the separate barrier element and/or wound packing. In using such a kit, the barrier element and/or wound packing may be attached to the medical dressing before the medical dressing is delivered to a patient. Alternatively, the barrier element and/or wound packing may be placed on or in the wound, with the medical dressing deployed over the wound after the barrier element and/or wound packing is/are in position.

Although the medical dressings of the present invention may be used to provide negative pressure wound therapy, in some instances fluids or other materials may potentially be delivered into the sealed environment through the medical dressing. For example, delivery devices such as pipettes, needles, etc. may be used to pierce the backing of the medical dressing, with the fluids or other materials delivered into the sealed environment through the delivery devices. It may be preferred that the delivery of materials into the sealed environment through the medical dressing does not functionally compromise the ability of the medical dressing to define a sealed environment as described herein.

To provide resealable access to the sealed environment through the medical dressing, the material used for the medical dressing backing may, for example, be self-sealing such that the opening formed through the backing seals upon removal of the delivery device (in the manner of, e.g., a septum). In other instances, a closure element may be applied over the external surface of the medical dressing backing after the delivery device is removed to close any opening formed through the backing by the delivery device.

Figure 9:
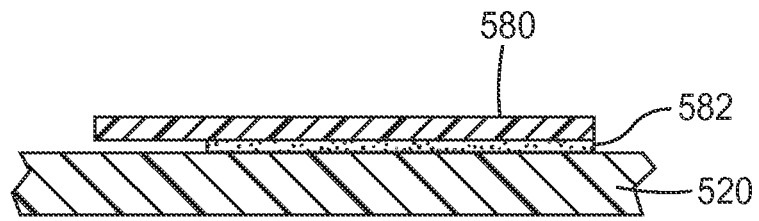
FIG. 9 is a cross-sectional view of an exemplary closure element that may be attached to the medical dressing.

FIG. 9 is a cross-sectional view of one potential closure element 580 attached to a backing 520 of a medical dressing of the present invention. As discussed herein, the closure element 580 is preferably attached to the backing 520 over an opening made to provide access to the sealed environment. The closure element 580 may preferably be attached to the backing 520 using a pressure sensitive adhesive 582.

Any closure element 580 may be attached to the medical dressing before use, i.e., the closure element 580 may be pre-attached to the backing 520 (or some other part of the medical dressing). If pre-attached, the closure element 580 can then be detached from its initial location and re-attached over an opening made through the backing 520 to provide access to the sealed environment.

Figure 10:
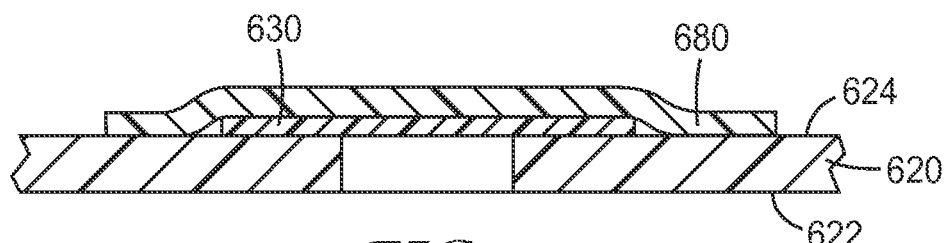
FIG. 10 is a cross-sectional view of another exemplary closure element attached to the medical dressing to seal the valve shut.

In some embodiments, a closure element may be attached to the external surface of the medical dressing over the valve, such that the valve is sealed shut by the closure element until the closure element is removed or otherwise opened. One such embodiment is depicted in FIG. 10, where a closure element 680 is attached to the external surface 624 of the backing 620 surrounding a valve 630.

The closure element 680 may be attached using adhesives, heat sealing, welding, casting, etc., although it may be preferred that the closure element 680 be attached using a pressure sensitive adhesive such that the closure element 680 can be reattached to the medical dressing after it is removed from its location over the valve 630. In such an embodiment, the closure element 680 may potentially be reattached to the medical dressing over the valve 630 to reseal the valve 630 and/or the closure element 680 may be attached elsewhere on the medical dressing to seal an opening made through the backing 620 to, e.g., deliver materials into the sealed environment as described herein.

Although the closure element is depicted and described as being attached to the external surface of the backing 620, it should be understood that the closure element 680 may simply be attached to the external surface of the valve 630 (which is essentially equivalent to the external surface of the medical dressing as a whole).

Figure 11:
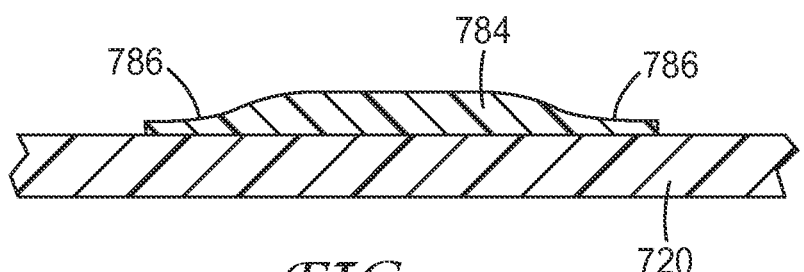
FIG. 11 is a cross-sectional view of an exemplary septum element attached to the medical dressing.

In still other embodiments, a septum element may be attached to the medical dressing backing to provide resealable access to the sealed environment through the medical dressing (e.g. a septum). FIG. 11 is a cross-sectional view of one potential septum element 784 attached to a backing 720 of a medical dressing of the present invention. As discussed herein, the septum element 784 is preferably attached to the backing 720 to provide a location through which a resealable opening is made to provide access to the sealed environment. The septum element 784 may preferably have a thicker central portion and tapered edges 786 to provide a gradual transition from the thicker central portion.

The septum element (or elements) 784 can be placed on the interior surface and/or the external surface of the backing 720. The septum element 784 may preferably be attached to the backing 720 using any suitable technique or combination of techniques, e.g., adhesives, heat sealing, welding, casting, etc.

The medical dressing can include only one or more than one septum element. The septum elements may, in some embodiments, be found on only one side of the backing or on both sides of the backing. In still other embodiments, one or more pairs of septum elements may be located on both the interior surface and the external surface of the backing, directly opposed from each other.

The septum elements 784 may be attached to the medical dressings before use, i.e., the septum elements 784 may be pre-attached to the backing 720 (or some other part of the medical dressing). In other embodiments, the septum elements 784 may be provided separately (i.e., unattached to the backing 720), thus allowing the end user to place the septum element 784 in a selected location on the backing 720, for example, as a pressure sensitive adhesive coated elastomeric septum that is adhered to the dressing where desired.

It is contemplated that fluids are delivered through the septum by inserting a tube similar to a vascular access catheter in which the catheter is inserted through the septum with the assistance of a blunt needle or introducer which is subsequently removed leaving behind the blunt end relatively flexible catheter tubing. In this manner, no needle remains in place which could potentially injure the patient.

Fluids delivered to the sealed environment through the medical dressing may include gases (e.g., oxygen, nitric oxide, ozone, etc.) and/or liquids (e.g., saline, water, etc.). Particulates may, in some instances, also be delivered to the sealed environment if, e.g., they are entrained within a fluid delivered into the sealed environment.

In some instances, it may be desirable to deliver one or more active agents to the sealed environment (and, thus, the wound covered by the dressing). The active agents may be provided as a fluid and/or may be carried within a fluid that is delivered to the internal volume. Some potentially suitable active agents may include, e.g., antimicrobials, antibiotics, analgesics, healing factors such as vitamins, growth factors, nutrients and the like. Examples of other potentially suitable agents may be described in U.S. Pat. No. 6,867,342.

If delivered, an active agent (or agents) could be supplied to the sealed environment continuously or intermittently. For example, an active agent could be delivered to the sealed environment and allowed to remain in place (i.e., resident) for a selected period of time (e.g., several hours) followed by, e.g., delivery of a second active agent, delivery of negative pressure therapy, etc. The initial active agent could be removed before delivery of the second agent or it could be allowed to remain in place. Alternatively, the sealed environment could be rinsed with, e.g., saline or another flushing solution before placing the sealed environment in a negative pressure condition, before delivery of a second agent, etc.

As discussed herein, the medical dressings of the present invention may be used for negative pressure wound therapy by providing a valve in the medical dressing through which fluid can be removed from a sealed environment defined by the medical dressing. The fluid is removed from the sealed environment through the valve using a pump that can preferably be periodically attached to the medical dressing. It may be preferred that the pump include a seat that can seal against the external surface of the backing of the medical dressing to provide a fluid-tight seal.

To remove fluid from the sealed environment, the pressure surrounding the exterior of the valve can be sufficiently reduced to open the valve and remove fluid from the sealed environment through the valve. It may be preferred that the valve be a normally-closed one-way valve such that the valve recloses when the reduced pressure environment is no longer present around the exterior of the valve (i.e., the pressure differential across the valve falls below the level needed to maintain the valve in the open configuration). As discussed herein, the negative pressure can preferably be maintained within the sealed environment defined by the medical dressing.

Two important feature of the valves described herein is the ability of the valve to open by the application of a differential (e.g., negative) pressure, and to remain functioning under the differential pressure conditions. Thus, if the vacuum were to fail, fluids removed from the wound would not re-enter the wound, as the valve would return to a closed position upon its failure.

The pumps used in connection with the medical dressings of the present invention may take any suitable form. In some embodiments, the pumps may be portable, self-contained devices, while in other embodiments the pumps may be fixed, stationary systems. In some instances, fluids may even be removed from a sealed environment defined by the medical dressings using suction developed by a person using their mouth (in, e.g., a battlefield or other remote location). In one embodiment the pump is a micropump as disclosed in Applicant's patent application, U.S. Ser. No. 61/042,698, filed on Apr. 4, 2008, and Applicant's copending patent application entitled WOUND DRESSING WITH MICROPUMP, PCT Application No. PCT/US09/39058, filed on Apr. 1, 2009, and incorporated by reference in its entirety.

Examples of some potentially suitable pumps that may be used with and/or supplied in a kit with the medical dressings of the present invention may include the pumps described in U.S. Patent Application Publication No. US 2007/0209326 (Tretina), although many other pumps may be used in place of the pumps disclosed therein. Although the pumps described in the document identified above include a power source (e.g., a battery), pumps used in connection with the present invention may be manually powered. Examples of some other potentially suitable manually powered pumps may include, e.g., devices that include resilient cavities that can be compressed and, when returning to their pre-compression states, provide a vacuum force at the inlet of the pump (e.g., bulbs, hemovacs, etc.).

In some embodiments, the kits of the present invention may preferably include one or more traps or fluid collection components capable of collecting and retaining liquids (and, in some embodiments, gases) removed from the sealed environments defined by the medical dressings. The traps may be integral with the pumps in some embodiments, while in other embodiments the traps may be separate from the pumps such that the traps may be replaced without requiring replacement of both the pumps and the traps. Examples of some potentially suitable traps that are designed to separate liquids from the removed fluids may be described in, e.g., U.S. Patent Application Publication Nos. US 2007/0209326 (Tretina) and US 2007/0172157 (Buchman).

It may be preferred that the medical dressings of the present invention and any pumps used therewith to remove fluids from sealed environments be capable of quickly connecting with each other to form a fluid-tight seal during removal of fluids from the sealed environments defined by the medical dressings. The medical dressing itself may preferably be featureless (e.g., present only the smooth external surface of the backing), while the pump includes a seat that provides a surface capable of sealing against the featureless backing to form the required fluid-tight seal.

In some embodiments, the medical dressings and pumps may include more conventional connections/fittings to provide a fluid-tight connection between the pumps and the medical dressings. Such fittings may be useful where, e.g., the pump is to be connected to the medical dressing for an extended period of time, e.g., for more than 2 minutes. In such an embodiment, the medical dressing kit may include a fitting that attaches to the external surface of the backing using, e.g., a pressure sensitive adhesive, etc. The fitting may, for example, include a tubing connector, Luer lock fitting, etc. designed for longer-term connection to a pump. The adhesive used to attach the fitting to the medical dressing may be releasable, i.e., the fitting may potentially be removed from the dressing while the dressing remains in place over a wound, such that any sealed environment defined by the medical dressing remains intact during removal of the fitting.

Figure 12:
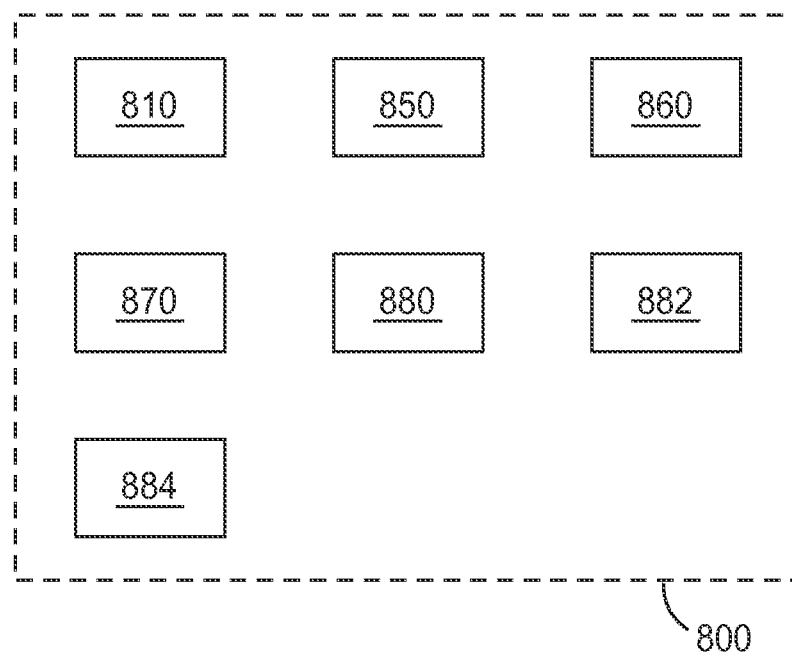
FIG. 12 is a block diagram of components that may be supplied in one exemplary embodiment of a medical dressing kit according to the present invention.

Medical Dressing Kits:

The medical dressings of the present invention may potentially be supplied in the form of a kit with one or more of the optional components. FIG. 12 is a schematic diagram of one kit 800. The kit 800 may preferably be provided in a sealed package (e.g., bag, pouch, tray, etc.). The kit 800 includes one or more medical dressings 810 of the present invention (with each medical dressing including one or more valves).

One or more stand-off elements 850 may also be provided in the kit 800, with the stand-off elements 850 attached to the medical dressing(s) 810 and/or provided as separate articles for the user to attach at their discretion. The kit 800 may also include one or more barrier elements 860 and/or wound packing material 870 as described herein.

The kit 800 may also include one or more pumps 880 that can be used in conjunction with the medical dressings 810. The kit 800 may also include one or more traps 882 that may be used with the one or more pumps 880 to retain fluids (e.g., liquids) that may be removed from sealed environments defined by the dressings 810 over wounds. In other embodiments, the kits 800 may include one or more fluid traps 882, but no pumps where, for example, the user has a reusable pump that can be used with the trap or traps 882 supplied in the kit 800 with the dressings 810. The kits 800 may also potentially include one or more fittings 884 adapted for attachment to the external surfaces of the dressings 810 as discussed herein, where the fittings 884 can be used to provide connections between the valves in the dressings 810 and the pumps 880.

The following discussions will provide some non-limiting examples as to the construction of the various features that may be provided in the medical dressings of the present invention.

Backings:

The medical dressings of the present invention are useful in connection with any conformable backing that provides a sufficiently impermeable barrier to the passage of liquids and at least some gases. Representative backings may include polymeric films and other familiar backing materials. The preferred backing materials may be translucent or transparent polymeric films.

The backings used in connection with the present invention may be high moisture vapor permeable film backings. Issued U.S. Pat. Nos. 3,645,835 and 4,595,001 describe methods of making such films and methods for testing their permeability. The film (and any adhesive used thereon as described herein) may transmit moisture vapor at a rate equal to or greater than human skin. The adhesive-coated film may, e.g., transmit moisture vapor at a rate of at least 300 g/m$^2$/24 hrs/37° C./100-10% RH, more preferably at least 700 g/m$^2$/24 hrs/37° C./100-10% RH, and most preferably at least 2000 g/m$^2$/24 hrs/37° C./100-10% RH using the inverted cup method as described in U.S. Pat. No. 4,595,001.

The backings may also preferably be conformable to anatomical surfaces. As such, when the backing is applied to an anatomical surface, it conforms to the surface even when the surface is moved. The backing may also be conformable to animal anatomical joints. When the joint is flexed and then returned to its unflexed position, the backing may stretch to accommodate the flexion of the joint, but is resilient enough to continue to conform to the joint when the joint is returned to its unflexed condition. A description of this characteristic of backings can be found in issued U.S. Pat. Nos. 5,088,483 and 5,160,315. Examples of some potentially suitable backings may include elastomeric polyurethane, polyester, or polyether block amide films. These films combine the desirable properties of resiliency, high moisture vapor permeability, and transparency.

Commercially available examples of potentially suitable backing materials may include the thin polymeric film backings sold under the tradenames TEGADERM (3M Company), BIOSITE (Johnson & Johnson Company), OPSITE (Smith & Nephew), etc. Many other backings may also be used, including those commonly used in the manufacture of surgical incise drapes (e.g., incise drapes manufactured by 3M Company under the tradename STERIDRAPE and IOBAN), etc.

Because fluids may be actively removed from the sealed environments defined by the medical dressings of the present invention, a relatively high moisture vapor permeable backing may not be required. As a result, some other potentially useful backing materials may include, e.g., metallocene polyolefins and SBS and SIS block copolymer (e.g., KRATON type) materials could be used.

Regardless, however, it may be preferred that the backings be kept relatively thin to, e.g., improve conformability. For example, it may be preferred that the backings be formed of (e.g., consist essentially of) polymeric films with a thickness of 200 micrometers or less, or 100 micrometers or less, potentially 50 micrometers or less, or even 25 micrometers or less.

Pressure Sensitive Adhesives:

The pressure sensitive adhesives that may preferably be used in the medical dressings of the present invention may include adhesives that are typically applied to the skin such as the acrylate copolymers described in U.S. Pat. No. RE 24,906, particularly a 96:4 iso-octyl acrylate:acrylamide copolymer. Another example may include a 70:15:15 isooctyl acrylate:ethyleneoxide acrylate:acrylic acid terpolymer, as described in U.S. Pat. No. 4,737,410 (Example 31). Other potentially useful adhesives are described in U.S. Pat. Nos. 3,389,827; 4,112,213; 4,310,509; and 4,323,557. Inclusion of medicaments or antimicrobial agents in the adhesive is also contemplated, as described in U.S. Pat. Nos. 4,310,509 and 4,323,557.

The pressure sensitive adhesives may, in some embodiments, transmit moisture vapor at a rate greater to or equal to that of human skin. While such a characteristic can be achieved through the selection of an appropriate adhesive, it is also contemplated in the present invention that other methods of achieving a high relative rate of moisture vapor transmission may be used, such as pattern coating the adhesive on the backing, as described in U.S. Pat. No. 4,595,001. Other potentially suitable pressure sensitive adhesives may include blown-micro-fiber (BMF) adhesives such as, for example, those described in U.S. Pat. No. 6,994,904. The pressure sensitive adhesive used in the medical dressing may also include one or more areas in which the adhesive itself includes structures such as, e.g., the microreplicated structures described in U.S. Pat. No. 6,893,655.

Release Liners:

Release liners may be supplied with the medical dressings of the present invention to protect the pressure sensitive adhesive used to attach the dressings to the patient and create the sealed environment. Release liners that may be suitable for use in the medical dressing of the present invention can be made of supercalendered kraft paper, glassine paper, polyethylene, polypropylene, polyester or composites of any of these materials. The liners are preferably coated with release agents such as fluorochemicals or silicones. For example, U.S. Pat. No. 4,472,480 describes low surface energy perfluorochemical liners. The liners may preferably be in the form of papers, polyolefin films, polyolefin coated paper or polyester films coated with silicone release materials. Examples of commercially available silicone coated release liners are POLY SLIK™ silicone release on polyolefin coated papers, FL2000™ silicone release on film, and STICK-NOT™ silicone release on supercalendered kraft paper, all available from Loparex Inc., (Willowbrook, Ill.); silicone coated supercalendered kraft paper from Akrosil, (Menasha, Wis.); and silicone release film from Huhtamaki Florchheim, (Florchheim, Germany). Another potential liner is silicone coated (1630) low density polyethylene available from Huhtamaki.

The selection of a specific release liner may be made in conjunction with the selection of a pressure sensitive adhesive. Those skilled in the art will be familiar with the processes of testing a new adhesive against different liners or a new liner against different adhesives to arrive at the combination of qualities desired in a final product. The considerations pertinent to the selection of a silicone release liner can be found in Chapter 18 of the *Handbook of Pressure Sensitive Adhesive Technology*, Van Nostrand-Reinhold, 1982, pp. 384-403. U.S. Pat. No. 4,472,480 also describes considerations pertinent to the selection of a perfluoropolyether release liner.

Carriers/Delivery Systems:

In some instances, the backings used in the medical dressings of the present invention may be so flexible and supple such that when a release liner is removed from the backing, the backing may tend to fold and adhere to itself, interfering with the smooth, aseptic application of the dressing to a patient's skin.

Various delivery systems have been proposed to address this problem such as those disclosed in U.S. Pat. No. 4,485,809; U.S. Pat. No. 4,600,001; and EPO Publication No. 0 051 935. Carrier-type delivery systems such as those described in U.S. Pat. No. 6,685,682 offer an alternative delivery system for use with conformable backings.

Alternative carriers and/or delivery systems may include frames, handles, stiffening strips, etc. as disclosed in issued U.S. Pat. Nos. 6,742,522; 5,979,450; 6,169,224; 5,088,483; 4,598,004; D 493,230; etc. Still another potentially suitable delivery system may be described in U.S. Patent Application Publication No. 2007/0156075 A1. In some instances, the backings can be delivered linerless as described in, e.g., U.S. Pat. No. 5,803,086.

The complete disclosure of the patents, patent documents, and publications cited herein are incorporated by reference in their entirety as if each were individually incorporated (although conflicts between any such disclosures and the descriptions explicitly provided herein should be resolved in favor of this document).

Exemplary embodiments of this invention are discussed and reference has been made to possible variations within the scope of this invention. These and other variations and modifications in the invention will be apparent to those skilled in the art without departing from the scope of the invention, and it should be understood that this invention is not limited to the exemplary embodiments set forth herein. Accordingly, the invention is to be limited only by the claims provided below and equivalents thereof.

The invention claimed is:

1. A medical dressing comprising:
    a backing comprising an interior surface and an external surface;
    adhesive on at least a portion of the interior surface, wherein the adhesive extends around a perimeter of the interior surface of the backing to adhere the medical dressing to a subject over a wound;
    a normally-closed valve attached to the backing over an opening formed through the backing, wherein fluid flow through the opening is controlled by the normally-closed valve, and wherein a dead volume between the normally-closed valve and the backing is 10 $mm^3$ or less;
        wherein, when the medical dressing is attached over the wound, the medical dressing defines a sealed environment over the wound, and further wherein application of a vacuum to the external surface of the backing over the normally-closed valve opens the normally-closed valve such that fluid within the sealed environment can be removed through the opening in the backing,
and wherein the normally-closed valve is flexible and comprises at least a flexible base layer that is attached to the backing and a flexible flap layer that is attached to the flexible base layer.

2. A medical dressing according to claim 1, wherein the normally-closed valve comprises a one-way normally-closed valve that permits fluid flow out of the sealed environment when in an open configuration and restricts fluid flow into the sealed environment when in a closed configuration.

3. A medical dressing according to claim 1, wherein the medical dressing further comprises a stand-off element, wherein the stand-off element defines plurality of fluid pathways to the opening on the interior surface of the backing when the stand-off element is positioned proximate the interior surface of the backing in the sealed environment.

4. A medical dressing according to claim 3, wherein the stand-off element comprises structures formed directly in the interior surface of the backing.

5. A medical dressing according to claim 3, wherein the stand-off element comprises a separate article attached to the interior surface of the backing.

6. A medical dressing according to claim 3, wherein the stand-off element comprises a separate article attached to the interior surface of the backing, and further wherein the stand-off element comprises fluid pathway-forming structures on two major surface of the separate article.

7. A medical dressing according to claim 1, wherein the medical dressing further comprises a septum element attached to the backing.

8. A medical dressing according to claim 1, wherein the medical dressing comprises a closure element attached to the medical dressing.

9. A medical dressing according to claim 1, wherein the medical dressing comprises a closure element attached to the medical dressing over the normally-closed valve, wherein the closure element seals the normally-closed valve shut.

10. A medical dressing according to claim 1, wherein the medical dressing further comprises a barrier element attached to the medical dressing proximate the interior surface of the backing.

11. A method of treating a wound, the method comprising:
applying a medical dressing over a wound,
wherein the medical dressing comprises:
a backing comprising an interior surface and an external surface,
adhesive on at least a portion of the interior surface, wherein the adhesive extends around a perimeter of the interior surface of the backing to adhere the medical dressing to a subject over a wound, and
a normally-closed valve attached to the backing over an opening formed through the backing, wherein fluid flow through the opening is controlled by the normally-closed valve, and wherein a dead volume between the normally-closed valve and the backing is 10 mm$^3$ or less, and
wherein, when the medical dressing is attached over the wound, the medical dressing defines a sealed environment over the wound, and further wherein application of a vacuum to the external surface of the backing over the normally-closed valve opens the normally-closed valve such that fluid within the sealed environment can be removed through the opening in the backing;
applying a vacuum to the external surface of the backing that opens the normally-closed valve in the medical dressing, and
removing fluid from the sealed environment through the normally-closed valve.

12. A method according to claim 11, wherein the fluid removed from the sealed environment comprises air such that a pressure within the sealed environment is below atmospheric pressure.

13. A method according to claim 11, wherein the fluid removed from the sealed environment comprises wound exudate from the wound.

* * * * *

UNITED STATES PATENT AND TRADEMARK OFFICE
CERTIFICATE OF CORRECTION

PATENT NO. : 9,572,962 B2
APPLICATION NO. : 12/936273
DATED : February 21, 2017
INVENTOR(S) : Matthew Scholz It is certified that error appears in the above-identified patent and that said Letters Patent is hereby corrected as shown below:

On the Title Page

Item [56], Line 1, delete "Internationat" and insert -- International --, therefor.

In the Specification

Column 16
Line 31, delete "application," and insert -- application (Attorney Docket No. 63832US002), --, therefor.
Line 33-34, delete "MICROPUMP," and insert -- MICROPUMP, (Attorney Docket No. 63832WO003), --, therefor.

Column 19
Line 34, delete "Florchheim, (Florchheim," and insert -- Forchheim, (Forchheim, --, therefor.

Signed and Sealed this
Seventh Day of November, 2017

Joseph Matal
*Performing the Functions and Duties of the*
*Under Secretary of Commerce for Intellectual Property and*
*Director of the United States Patent and Trademark Office*